(12) United States Patent
Kawashima et al.

(10) Patent No.: US 12,260,962 B2
(45) Date of Patent: Mar. 25, 2025

(54) PHYSIOLOGICAL INFORMATION ACQUISITION DEVICE, PROCESSING DEVICE, AND RECORDING MEDIUM

(71) Applicant: NIHON KOHDEN CORPORATION, Tokyo (JP)

(72) Inventors: Takuya Kawashima, Tokorozawa (JP); Wataru Matsuzawa, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 473 days.

(21) Appl. No.: 17/712,514

(22) Filed: Apr. 4, 2022

(65) Prior Publication Data

US 2022/0336105 A1    Oct. 20, 2022

(30) Foreign Application Priority Data

Apr. 14, 2021 (JP) .................................. 2021-068291

(51) Int. Cl.
*G16H 50/30* (2018.01)
(52) U.S. Cl.
CPC .................................. *G16H 50/30* (2018.01)
(58) Field of Classification Search
CPC ...................................................... G16H 50/30
USPC ......................................................... 600/301
See application file for complete search history.

(56) References Cited

U.S. PATENT DOCUMENTS

| 5,509,421 A * | 4/1996 | Muller ...................... A61B 8/02 |
| | | 600/300 |
| 2015/0164349 A1 | 6/2015 | Gopalakrishnan et al. |
| 2015/0265164 A1 | 9/2015 | Gopalakrishnan et al. |
| 2017/0238814 A1 | 8/2017 | Gopalakrishnan et al. |
| 2019/0038148 A1 * | 2/2019 | Valys ................. A61B 5/02405 |
| 2019/0038149 A1 | 2/2019 | Gopalakrishnan et al. |
| 2019/0076031 A1 | 3/2019 | Valys et al. |
| 2019/0104951 A1 | 4/2019 | Valys et al. |

(Continued)

FOREIGN PATENT DOCUMENTS

| JP | 2009100934 A | 5/2009 |
| JP | 2020-536623 A | 12/2020 |

(Continued)

OTHER PUBLICATIONS

Communication dated Dec. 12, 2022 issued by the European Patent Office in counterpart European Patent Application No. 22164354.7.

(Continued)

*Primary Examiner* — Nadia A Mahmood
(74) *Attorney, Agent, or Firm* — Sughrue Mion, PLLC

(57) ABSTRACT

A physiological information acquisition device configured to acquire physiological information of a subject includes: an input interface configured to receive waveform data corresponding to a measurement waveform of the physiological information from a sensor; a prediction unit configured to extract a feature from the waveform data using a convolutional neural network and predict a probability of the waveform data being classified into each of a plurality of classes; an importance specification unit configured to specify an importance of the feature with respect to a prediction result of the probability for at least one of the plurality of classes; and an output unit configured to output an indicator indicating the importance together with the measurement waveform.

10 Claims, 7 Drawing Sheets

(56) References Cited

U.S. PATENT DOCUMENTS

| | | |
|---|---|---|
| 2020/0022594 A1 | 1/2020 | Gopalakrishnan et al. |
| 2020/0107733 A1 | 4/2020 | Valys et al. |
| 2020/0229713 A1 | 7/2020 | Gopalakrishnan et al. |
| 2020/0281485 A9 | 9/2020 | Valys et al. |
| 2023/0099854 A1 | 3/2023 | Gopalakrishnan et al. |
| 2024/0099593 A1 | 3/2024 | Valys et al. |

FOREIGN PATENT DOCUMENTS

| | | |
|---|---|---|
| WO | 2020/049267 A1 | 3/2020 |
| WO | 2020/193778 A1 | 10/2020 |
| WO | 2020/226534 A1 | 11/2020 |

OTHER PUBLICATIONS

P. Garg et al., "Automatic 1D Convolutional Neural Network-based Detection of Artifacts in MEG acquired without Electrooculography or Electrocardiography", 2017 International Workshop on Pattern Recognition in Neuroimaging (PRNI), IEEE, Jun. 2017, DOI: 10.1109/PRNI.2017.7981506, (4 pages total).

Akshay Sujatha Ravindran et al., "Emotion Recognition by Point Process Characterization of Heartbeat Dynamics", 2019 IEEE Healthcare Innovations and Point of Care Technologies (HI-POCT), IEEE, Nov. 2019, DOI: 10.1109/HI-POCT45284.2019.8962886, (4 pages total).

Office Action issued Oct. 22, 2024 by the Japan Patent Office in Japanese Patent Application No. 2021-068291.

* cited by examiner

PHYSIOLOGICAL INFORMATION ACQUISITION DEVICE, PROCESSING DEVICE, AND RECORDING MEDIUM

CROSS-REFERENCE TO RELATED APPLICATIONS

This application is based on and claims priority under 35 USC 119 from Japanese Patent Application No. 2021-068291 filed on Apr. 14, 2021, the contents of which are incorporated herein by reference.

TECHNICAL FIELD

The presently disclosed subject matter relates to a device for acquiring physiological information of a subject. The presently disclosed subject matter relates to a processing device for processing the physiological information, and a non-transitory computer-readable recording medium storing a computer program executable by a processor of the processing device.

BACKGROUND ART

JP-A-2009-100934 discloses a device for measuring a pulse wave, which is an example of physiological information of a subject. A notification is sent to a user when it is determined that noise of no less than a predetermined level is mixed in a measurement waveform of a pulse wave acquired from a sensor.

An object of the presently disclosed subject matter is to enhance interpretation of a processing result of physiological information performed using a deep learning technique.

SUMMARY

A first aspect of the presently disclosed subject matter relates to a physiological information acquisition device configured to acquire physiological information of a subject including: an input interface configured to receive waveform data corresponding to a measurement waveform of the physiological information from a sensor; a prediction unit configured to extract a feature from the waveform data using a convolutional neural network and predict a probability of the waveform data being classified into each of a plurality of classes; an importance specification unit configured to specify an importance of the feature with respect to a prediction result of the probability for at least one of the plurality of classes; and an output unit configured to output an indicator indicating the importance together with the measurement waveform.

A second aspect of the presently disclosed subject matter relates to a processing device configured to process physiological information of a subject, the processing device comprising: an input interface configured to receive waveform data corresponding to a measurement waveform of the physiological information from a sensor; and one or more processors configured to extract a feature from the waveform data using a convolutional neural network to predict a probability of the waveform data being classified into each of a plurality of classes, specify an importance of the feature with respect to a prediction result of the probability for at least one of the plurality of classes, and cause an output device to output the prediction result and an indicator indicating the importance together with the measurement waveform.

A third aspect of the presently disclosed subject matter relates to a non-transitory computer-readable recording medium storing a computer program for causing one or more processors to execute a process. The process includes: receiving waveform data corresponding to a measurement waveform of the physiological information from a sensor; extracting a feature from the waveform data using a convolutional neural network to predict a probability of the waveform data being classified into each of a plurality of classes; specifying an importance of the feature with respect to a prediction result of the probability for at least one of the plurality of classes; and causing an output device to output the prediction result and an indicator indicating the importance together with the measurement waveform.

BRIEF DESCRIPTION OF DRAWINGS

Exemplary embodiments of the present invention will be described in detail based on the following figures, wherein.

DESCRIPTION OF EMBODIMENTS

Exemplary embodiments will be described in detail below with reference to the accompanying drawings.

Figure 1:
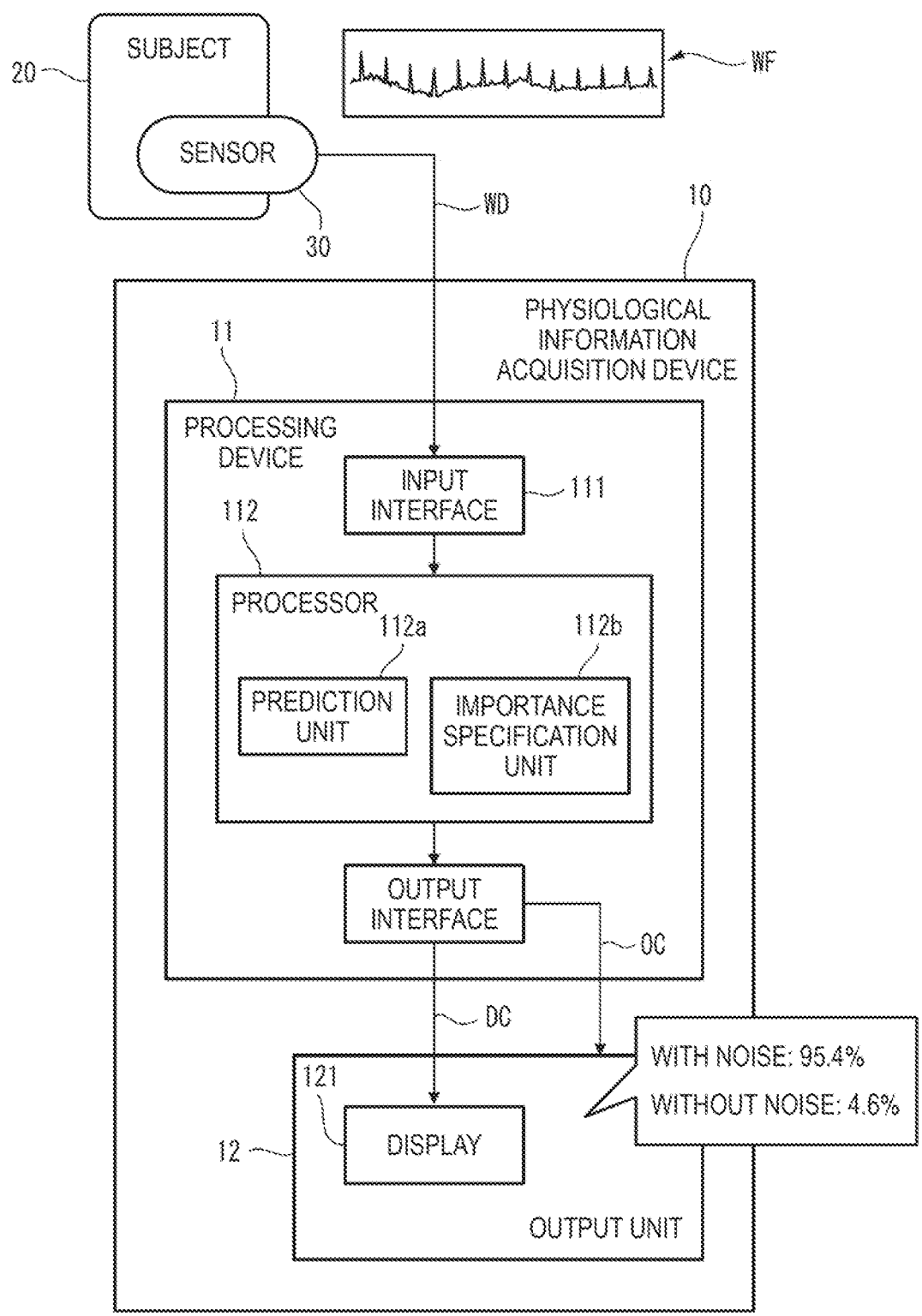
FIG. 1 illustrates a configuration of a physiological information acquisition device according to an embodiment.

FIG. 1 illustrates a configuration of a physiological information acquisition device 10 according to an embodiment. The physiological information acquisition device 10 is configured to acquire an electrocardiogram of a subject 20. The electrocardiogram is an example of physiological information.

The physiological information acquisition device 10 can include a processing device 11. The processing device 11 is configured to process the electrocardiogram of the subject 20 acquired by the physiological information acquisition device 10.

The processing device 11 can include an input interface 111. The input interface 111 is configured to receive waveform data WD corresponding to a measurement waveform WF of the electrocardiogram of the subject 20 through a sensor 30. The waveform data WD corresponds to a change over time of a measured cardiac potential. The waveform data WD may be either in a form of analog data or in a form of digital data in accordance with a specification of the sensor 30. When the waveform data WD is in the form of analog data, the input interface 111 can include an appropriate conversion circuit including an A/D converter.

The processing device 11 can include a processor 112. The processor 112 may be implemented by a general-purpose microprocessor that operates in cooperation with a general-purpose memory. Examples of the general-purpose microprocessor include a CPU (Central Processing Unit), an MPU (Micro-processing unit), and a GPU (Graphics Processing Unit). Examples of the general-purpose memory include a ROM (Read Only Memory) and a RAM (Random Access Memory). In this case, a ROM may store a computer program that executes the above-described processing. The ROM is an example of a non-transitory computer-readable medium storing a computer program. The general-purpose microprocessor specifies at least a part of the program stored in the ROM, loads the program into the RAM, and executes the above-described processing in cooperation with the RAM. The computer program may be pre-installed in the general-purpose memory, or may be downloaded from an external server via a communication network and installed in the general-purpose memory. In this case, the external server is an example of a non-transitory computer-readable medium storing a computer program.

The processor 112 may be realized by a dedicated integrated circuit capable of executing the above-mentioned computer program, such as a microcontroller, an ASIC (Application Specific Integrated Circuit), or an FPGA (Field Programmable Gate Array). In this case, the above computer program is pre-installed in a storage device included in the dedicated integrated circuit. The storage device is an example of a computer-readable medium storing a computer program. The processor 112 may also be realized by a combination of a general-purpose microprocessor and a dedicated integrated circuit.

The processor 112 can execute the above-described computer program to operate as a prediction unit 112a. The prediction unit 112a is configured to extract features from the waveform data WD using a convolutional neural network (CNN) to predict a probability of the waveform data WD being classified into each of a plurality of classes. Examples of the CNN include GoogleNet, ResNet, LeNet, AlexNet, and VGG.

In this example, the waveform data WD is classified into a "without noise" class and a "with noise" class. The "without noise" class corresponds to a state determined as without noise overlapping the measurement waveform WF of the electrocardiogram acquired from the subject 20. The "with noise" class corresponds to a state determined as having noise overlapping the measurement waveform WF of the electrocardiogram acquired from the subject 20.

The CNN is a learned model obtained by learning in advance using, as training data, a large amount of waveform data corresponding to measurement waveforms of electrocardiograms known as overlapped with noise, and a large amount of waveform data corresponding to measurement waveforms of electrocardiograms known as without being overlapped with noise. Specifically, at least one of a weight value and a bias value in a feature extraction layer or a classification layer is adjusted so as to reduce a difference between the prediction result output from the CNN and a correct answer.

Therefore, the feature in the present example corresponds to a part of the measurement waveform WF whose shape serves as a clue for obtaining the prediction result.

The physiological information acquisition device 10 can include an output unit 12. The processing device 11 can include an output interface 113. The processor 112 is configured to output an output control signal OC for causing the output unit 12 to output the prediction result obtained by the prediction unit 131 from the output interface 113. The output control signal OC may be an analog signal or a digital signal according to a specification of the output unit 12. In a case where the output control signal OC is an analog signal, the output interface 113 can include an appropriate conversion circuit including a D/A converter.

The output unit 12 is a user interface for notifying the user of the prediction result obtained by the prediction unit 131 based on the output control signal OC. The prediction result is output through at least one of a visual notification, an auditory notification, and a tactile notification. The output unit 12 is an example of an output device. The output unit 12 can include a display 121. The display 121 may be used when the prediction result is to be output through a visual notification.

In the example illustrated in FIG. 1, a probability of noise overlapping the measurement waveform WF of the electrocardiogram acquired from the subject 20 is predicted as 95.4%, and a probability of no noise overlapping the measurement waveform WF is predicted as 4.6%.

The processor 112 can execute the above-described computer program to operate as an importance specification unit 112b. The importance specification unit 112b is configured to use gradient weighted class activation mapping (Grad-CAM) to specify an importance with respect to the prediction result of the feature extracted by the prediction unit 112a.

The importance specification unit 112b is configured to apply Grad-CAM to at least one of the plurality of classes used for classification by the prediction unit 112a. That is, in the above example, Grad-CAM is applied to at least one of the "with noise" class and the "without noise" class.

Figure 2:
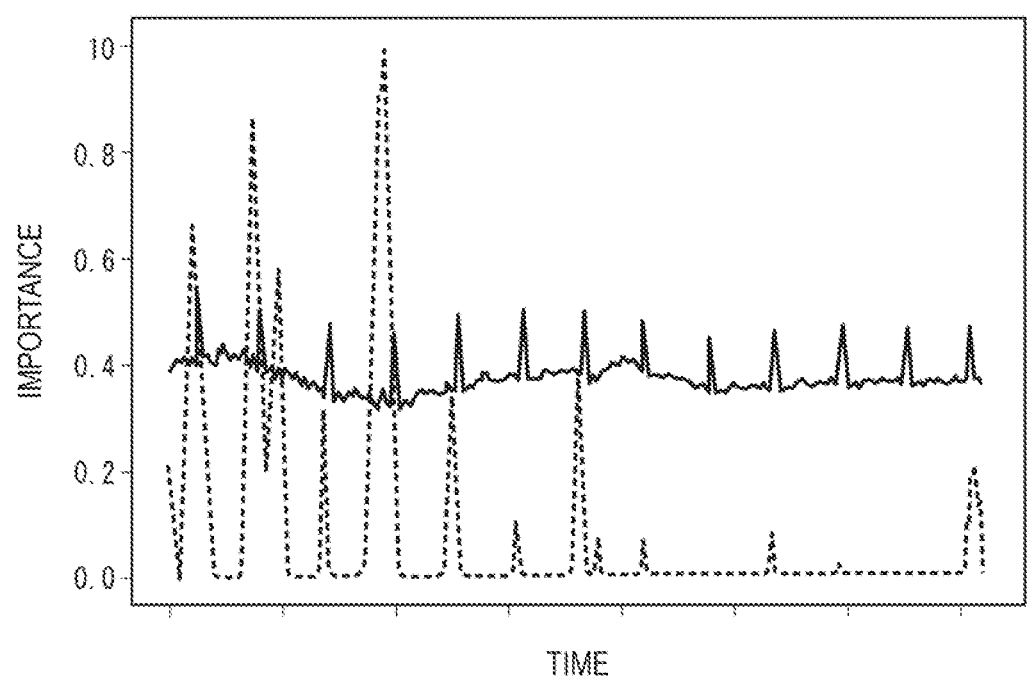
FIG. 2 illustrates an importance specified by an importance specification unit in FIG. 1.

FIG. 2 illustrates a case where Grad-CAM is applied to the "with noise" class. The broken line represents the specified importance. The importance is illustrated as a probability taking a value of 0 to 1 or 0% to 100%. That is, in this example, the importance of each feature extracted by the prediction unit 112a is specified with respect to the prediction result that the probability of noise overlapping the measurement waveform WF of the electrocardiogram acquired from the subject 20 is 95.4%.

Specifically, for each feature extracted by the prediction unit 112a, the value of the waveform data WD corresponding to the part of the measurement waveform WF according to the feature is changed by the same amount, and a variation in the prediction result (probability value) caused by the change is observed. A feature that causes a larger change in probability value due to the change is determined as having a larger importance.

The above processing can specify which portion of the measurement waveform WF illustrated in FIG. 2 has a higher importance with respect to the prediction result of the probability of being overlapped with noise.

The processor 112 is configured to output, from the output interface 113, a display control signal DC for causing the display 121 to display a color indicating the importance specified by the importance specification unit 112b together with the measurement waveform WF. The display control signal DC may be an analog signal or a digital signal according to a specification of the display 121. Ina case where the display control signal DC is an analog signal, the output interface 113 can include an appropriate conversion circuit including a D/A converter.

Figure 3:
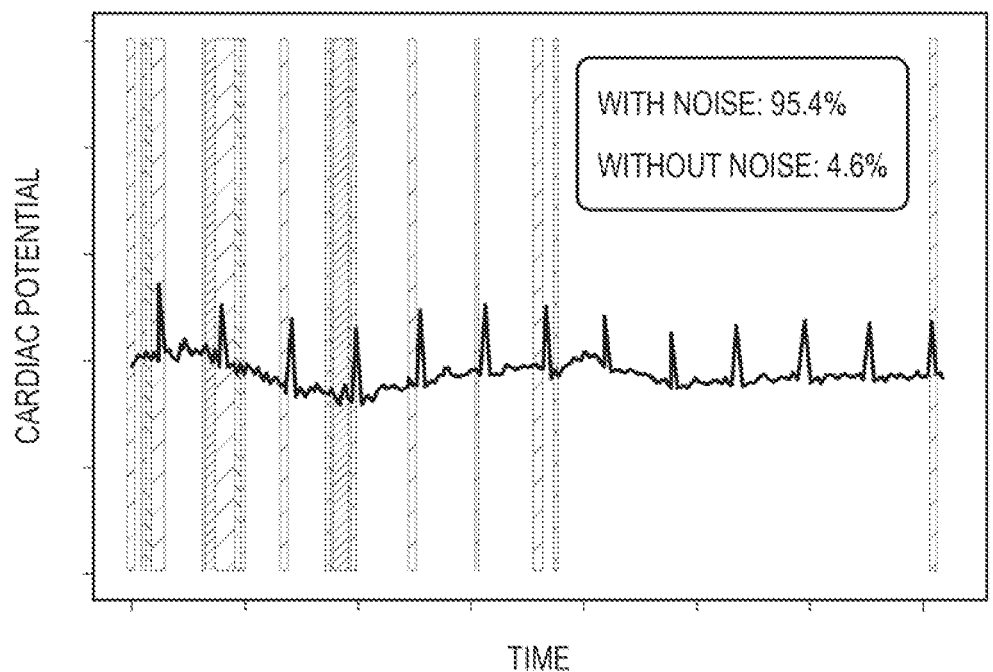
FIG. 3 illustrates a display example on a display in FIG. 1.

As illustrated in FIG. 3, the display 121 may be configured to display the color indicating the importance specified by the importance specification unit 112b in a manner overlapping the measurement waveform WF, based on the display control signal DC. In this example, the prediction result that the probability of "with noise" is 95.4% has a higher importance, and thus is assigned with a darker color. In an example of the drawing, a color is assumed to be darker if a pattern has more hatched lines. The "darker color" may be realized by changing a brightness or a chroma of a specific color, or may be realized by using another color having a hue that can be recognized as a darker color. The color is an example of an indicator.

The importance may be divided into a plurality of numerical ranges. In this case, at least one of different colors and different patterns may be assigned to the numerical ranges to distinguish the plurality of numerical ranges from each other. The pattern is also an example of an indicator.

Use of deep learning model has been attempted for determination on physiological information of a subject. On the other hand, when a deep learning model is used, it is theoretically difficult to obtain a clear basis for the prediction result. In the medical field, there is a tendency of avoiding ambiguous basis for determination.

With the configuration according to the present embodiment, it is possible to use a convolutional neural network, which is a deep learning technique, for determination performed on physiological information, while visually presenting information that can serve as basis for prediction to a user through an indicator indicating which portion of the measurement waveform contributes to the determination, so that the user can be entrusted with interpretation or verification of the determination result. For example, in the case of the example illustrated in FIG. 3, the user can intensively check a part of the measurement waveform WF corresponding to a position displayed in a dark color, thereby verifying whether the prediction result by the prediction unit 112a is valid. Therefore, it is possible to enhance interpretation of a processing result of the physiological information performed using the deep learning technique.

Another example of processing that can be executed in the physiological information acquisition device 10 will be described with reference to FIGS. 4 to 7.

Figure 4:
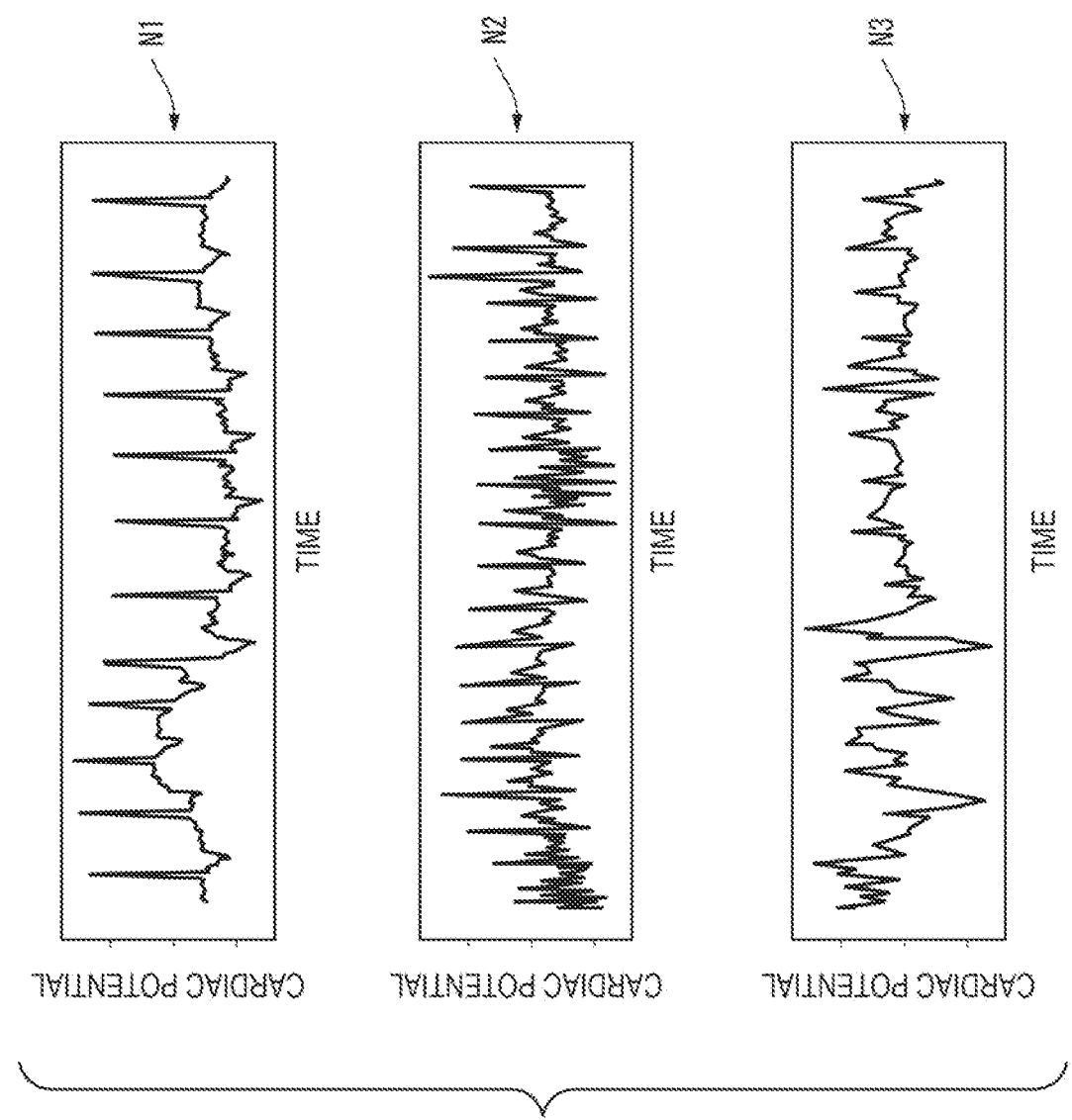
FIG. 4 illustrates a measurement waveform of an electrocardiogram overlapped with noise.

FIG. 4 illustrates a measurement waveform of an electrocardiogram overlapped with noise. A measurement waveform N1 is an example of a measurement waveform overlapped with noise derived from baseline drift. A measurement waveform N2 is an example of a measurement waveform overlapped with myoelectric noise. A measurement waveform N3 is an example of a measurement waveform overlapped with noise caused by deterioration of electrode, positional deviation, or the like.

The prediction unit 112a according to the present example extracts a feature from the waveform data WD corresponding to the measurement waveform WF of the electrocardiogram acquired from the subject 20, and predicts a probability of the waveform data WD being classified into each of the "without noise" class, a "baseline drift noise" class, a "myoelectric noise" class, and an "electrode noise" class. The "baseline drift noise" class corresponds to a state determined as having noise derived from baseline drift overlapping the measurement waveform WF of the electrocardiogram acquired from the subject 20. The "myoelectric noise" class corresponds to a state determined as having myoelectric noise overlapping the measurement waveform WF of the electrocardiogram acquired from the subject 20. The "electrode noise" class corresponds to a state determined as having noise derived from electrode overlapping the measurement waveform WF of the electrocardiogram acquired from the subject 20.

Figure 5:
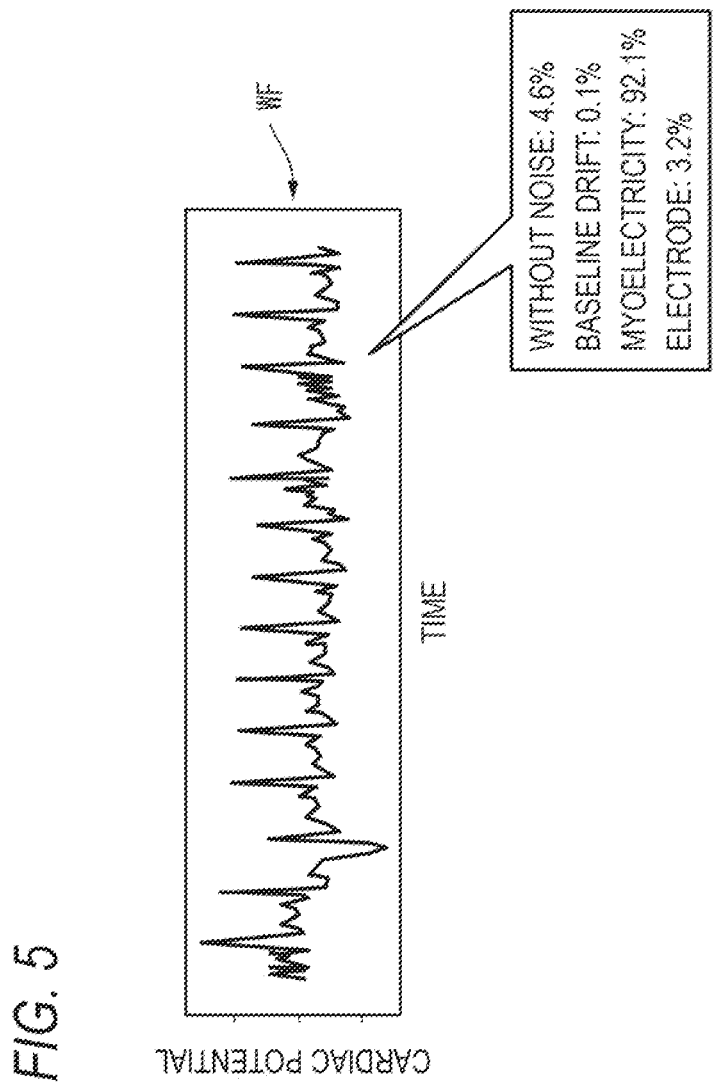
FIG. 5 illustrates an example of processing performed by a prediction unit in FIG. 1.

In the example illustrated in FIG. 5, a probability of no noise overlapping the measurement waveform WF of the electrocardiogram acquired from the subject 20 is predicted as 4.6%. A probability of noise derived from baseline drift overlapping the measurement waveform WF of the electrocardiogram acquired from the subject 20 is predicted as 0.1%. A probability of myoelectric noise overlapping the measurement waveform WF of the electrocardiogram acquired from the subject 20 is predicted as 92.1%. A probability of noise derived from electrode overlapping the measurement waveform WF of the electrocardiogram acquired from the subject 20 is predicted as 3.2%. That is, the prediction unit 112a predicts that noise overlaps the measurement waveform WF of the electrocardiogram acquired from the subject 20 and that the noise is substantially myoelectric noise.

The importance specification unit 112b according to the present example applies Grad-CAM to the prediction result relating to each of the "baseline drift noise" class, the "myoelectric noise" class, and the "electrode noise" class, and specifies the importance with respect to the prediction result relating to each class of the feature of the waveform data WD extracted by the prediction unit 112a.

Figure 6:
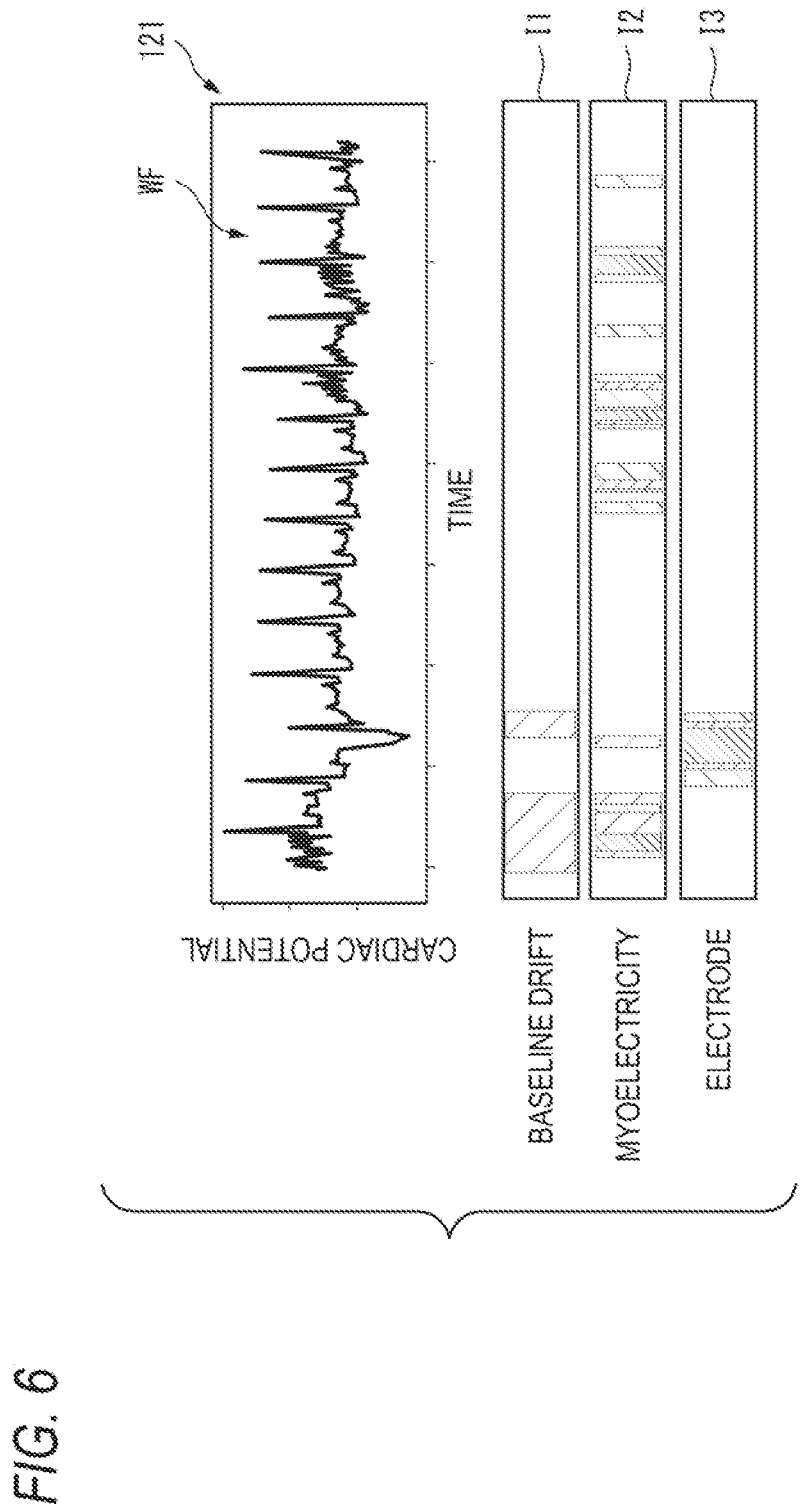
FIG. 6 illustrates a display example on a display based on the processing in FIGS. 4 and 5.

As a result, as illustrated in FIG. 6, an indicator I1 indicating the importance of the feature with respect to the probability of the measurement waveform WF being classified into the "baseline drift noise" class, an indicator I2 indicating the importance of the feature with respect to the probability of the measurement waveform WF being classified into the "myoelectric noise" class, and an indicator I3 indicating the importance of the feature with respect to the probability of the measurement waveform WF being classified into the "electrode noise" class are displayed on the display 121 together with the measurement waveform WF.

The indicator I1, the indicator I2, and the indicator I3 can each include a color corresponding to the specified importance. Same or similarly to the example illustrated in FIG. 3, a higher importance is assigned with a darker color. In an example of the drawing, a color is assumed to be darker if a pattern has more hatched lines. However, the color depth is determined based on a relative level of the importance in each class, and does not indicate an absolute level of the importance over all the classes.

One of the "baseline drift noise" class, the "myoelectric noise" class, and the "electrode noise" class may be an example of a first class. In this case, another one of the "baseline drift noise" class, the "myoelectric noise" class, and the "electrode noise" class may be an example of a second class.

Here, the probability of the waveform data WD predicted by the prediction unit 112a being classified into the first class is an example of a first prediction result. The importance with respect to the first prediction result of the feature specified by the importance specification unit 112b is an example of a first importance. The indicator indicating the first importance is an example of a first indicator.

Same or similarly, the probability of the waveform data WD predicted by the prediction unit 112a being classified into the second class is an example of a second prediction result. The importance with respect to the second prediction result of the feature specified by the importance specification unit 112b is an example of a second importance. The indicator indicating the second importance is an example of a second indicator.

The configuration according to the present example provides an indicator indicating the importance of the feature with respect to the prediction result for each of the plurality of classes provided for classification by the prediction unit 112a. Therefore, the user can verify whether the prediction result obtained by the prediction unit 112a is valid for a plurality of noise cause candidates. For example, it is possible not only to check which part of the measurement waveform WF contributes to the determination that the probability of being overlapped with myoelectric noise is the highest, but also to check which part of the measurement waveform WF contributes to the determination that there is a possibility of being overlapped with electrode noise. This enables more polygonal interpretation and verification with respect to the determination made by using the deep learning technique.

In this example, the indicator I1, the indicator I2, and the indicator I3 are displayed on the display 121 in a manner without overlapping the measurement waveform WF.

Such a configuration can limit a decrease in visibility of the measurement waveform WF due to the plurality of indicators being displayed on the display 121. The display method according to the present example can also be applied to the example in FIG. 3 in which an indicator is provided for a single class.

Figure 7:
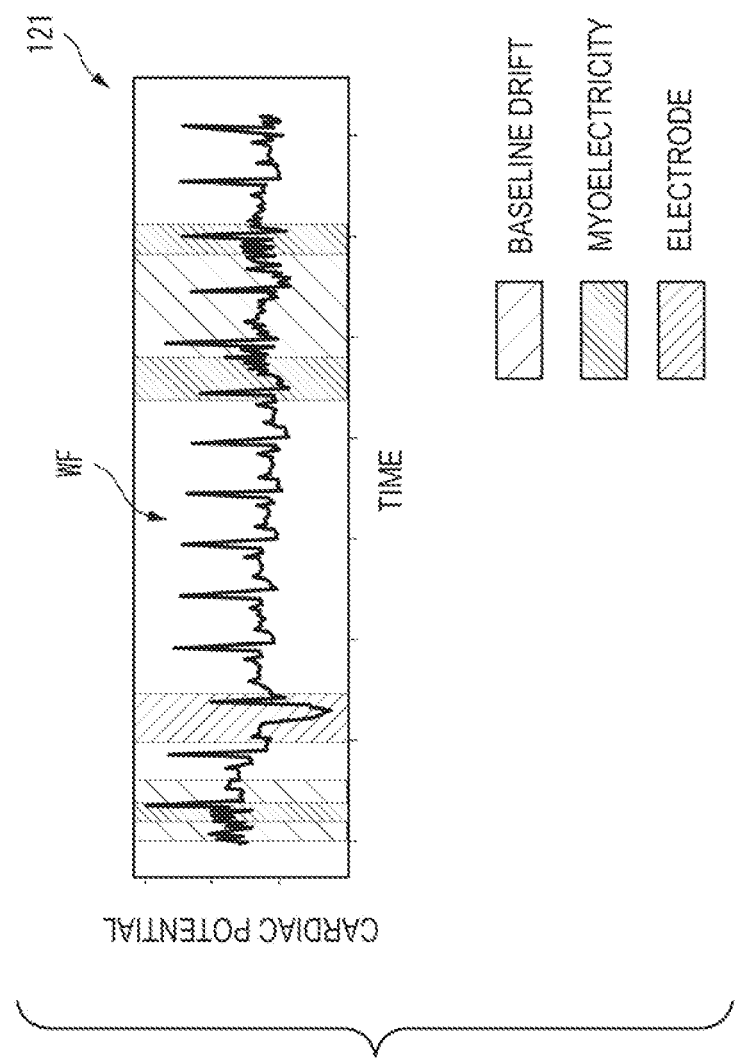
FIG. 7 illustrates another display example on the display based on the processing in FIGS. 4 and 5.

On the other hand, as illustrated in FIG. 7, a plurality of indicators assigned with different colors for the respective classes may be displayed in a manner overlapping the measurement waveform WF. For example, an indicator having a first color is assigned for indicating the importance of the feature with respect to the prediction result related to the "baseline drift noise" class. An indicator having a second color is assigned for indicating the importance of the feature with respect to the prediction result related to the "myoelectric noise" class. An indicator having a third color is assigned for indicating the importance of the feature with respect to the prediction result related to the "electrode noise" class. The expression "different colors" used in the present specification means colors each having at least one of a different hue, brightness, and chroma.

Different patterns may also be assigned to the plurality of classes as long as the classes can be distinguished from each other.

In this case, in order to limit a decrease in the visibility of the measurement waveform WF due to the plurality of indicators being displayed in a manner overlapping each other, the indicators are preferably displayed only for a region corresponding to a feature having an importance exceeding a threshold value.

The above embodiment is merely an example for facilitating understanding of the presently disclosed subject matter. The configurations according to the above embodiment can be appropriately changed or improved without departing from the gist of the presently disclosed subject matter.

In the above-described embodiment, the indicators displayed on the display 121 can include colors that change according to the importance specified by the importance specification unit 112b. However, a graph display used in FIG. 2 can also be adopted as indicators for indicating the importance. In this case, the indicator may be displayed in a manner overlapping the measurement waveform WF or may be displayed in a manner without overlapping the measurement waveform WF.

The measurement waveform WF may be partially displayed in a different mode according to the importance specified by the importance specification unit 112b. For example, a part of the measurement waveform WF determined as having a high importance may be emphasized by using a different color or line type, or by blinking. Such a display mode is also an example of an indicator.

Figure 8:
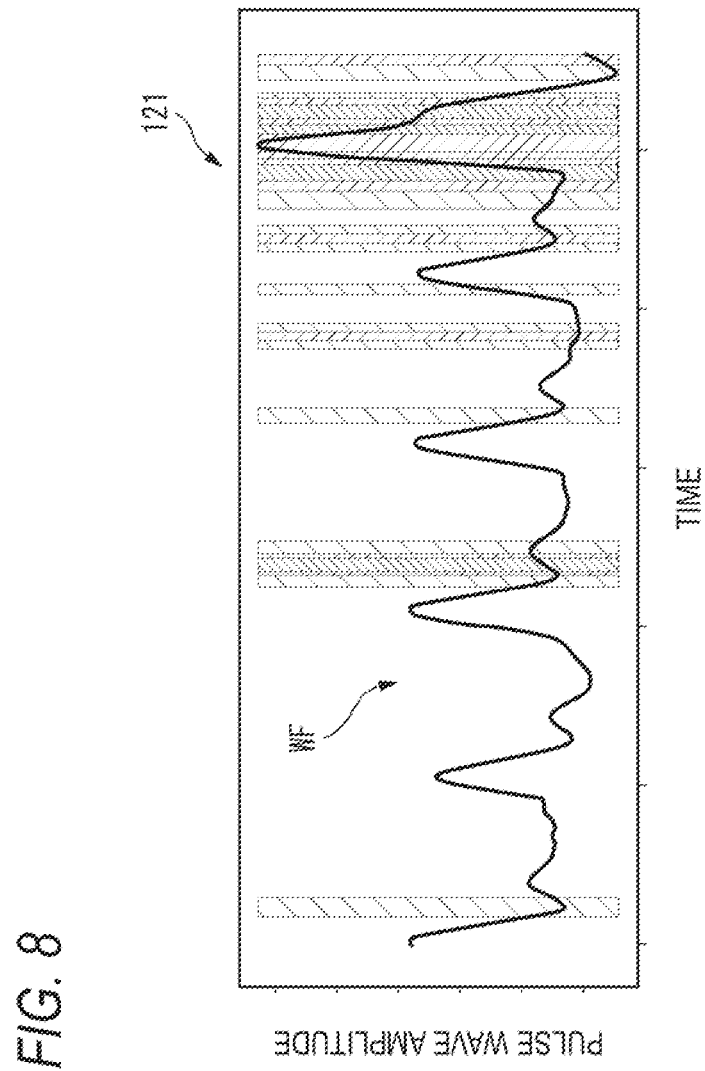
FIG. 8 illustrates another display example on the display in FIG. 1.

The physiological information of the subject 20 acquired by the physiological information acquisition device 10 is not limited to the electrocardiogram. The presence or absence of overlapping noise and the type of overlapping noise may also be predicted for measurement waveforms of pulse wave, electroencephalogram, invasive blood pressure, and respiration. FIG. 8 illustrates an example in which, in a case where a measurement waveform WF of pulse wave is predicted as being overlapped with noise based on a feature extracted from the measurement waveform WF, an indicator indicating an importance of the feature with respect to the prediction result is displayed on the display 121.

Specifically, a color corresponding to the importance is displayed as an indicator in a manner overlapping the measurement waveform WF. Same or similarly to the example in FIG. 3, a higher importance is assigned with a darker color. In an example of the drawing, a color is assumed to be darker if a pattern has more hatched lines.

A target of prediction by the prediction unit 112a is not limited to the presence or absence of overlapping noise. For example, the target of prediction may be the acquired physiological information and the presence or absence of a symptom associated with the physiological information. The presence or absence of the symptom is an example of a plurality of classes. Examples of the combination of the physiological information and the symptom include electrocardiogram and atrial fibrillation, pulse wave and arrhythmia, electroencephalogram and epilepsy seizure, invasive blood pressure and hypertension, and respiration and apnea syndrome.

In the above-described embodiment, the prediction unit 112a and the importance specification unit 112b are described as functional modules realized by the same processor 112. However, the processor that implements the function of the prediction unit 112a and the processor that implements the function of the importance specification unit 112b may be different from each other.

In the above embodiment, the output unit 12 for outputting the prediction result and the indicator together with the measurement waveform WF is mounted on the physiological information acquisition device 10. However, the function of the output unit 12 can be realized in an independent output device capable of data communication with the physiological information acquisition device 10 via a communication network. In this case, the processor 112 of the processing device 11 transmits, from the output interface 113, the output control signal OC and the display control signal DC for causing the output device to display the notification of the prediction result, the measurement waveform WF, and the indicator.

In the above-described embodiment, the processing device 11 is mounted on the physiological information acquisition device 10. However, the function of the processing device 11 may be at least partially realized by a processor mounted on a cloud server device capable of data communication with the physiological information acquisition device 10 via a communication network. In this case, the waveform data WD may be transmitted from the sensor 30 or the physiological information acquisition device 10 to the cloud server device, so that the processor can execute the prediction processing and the importance identification processing. The processor transmits the output control signal OC and the display control signal DC for causing the physiological information acquisition device 10 to display the notification of the prediction result, the measurement waveform WF, and the indicator to the physiological information acquisition device 10 from the cloud server device. The physiological information acquisition device 10 performs an operation based on the received output control signal OC and display control signal DC. The device that executes the operation based on the output control signal OC and the display control signal DC transmitted from the cloud server device may be an output device independent of the physiological information acquisition device 10.

The presently disclosed subject matter is summarized as follows.

A first aspect of the presently disclosed subject matter relates to a physiological information acquisition device configured to acquire physiological information of a subject including: an input interface configured to receive waveform data corresponding to a measurement waveform of the physiological information from a sensor; a prediction unit configured to extract a feature from the waveform data using a convolutional neural network and predict a probability of the waveform data being classified into each of a plurality of classes; an importance specification unit configured to specify an importance of the feature with respect to a prediction result of the probability for at least one of the plurality of classes; and an output unit configured to output an indicator indicating the importance together with the measurement waveform.

A second aspect of the presently disclosed subject matter relates to a processing device configured to process physiological information of a subject, the processing device comprising: an input interface configured to receive waveform data corresponding to a measurement waveform of the physiological information from a sensor; and one or more processors configured to extract a feature from the waveform data using a convolutional neural network to predict a probability of the waveform data being classified into each of a plurality of classes, specify an importance of the feature with respect to a prediction result of the probability for at least one of the plurality of classes, and cause an output device to output the prediction result and an indicator indicating the importance together with the measurement waveform.

A third aspect of the presently disclosed subject matter relates to a non-transitory computer-readable recording medium storing a computer program for causing one or more processors to execute a process. The process includes: receiving waveform data corresponding to a measurement waveform of the physiological information from a sensor; extracting a feature from the waveform data using a convolutional neural network to predict a probability of the waveform data being classified into each of a plurality of classes; specifying an importance of the feature with respect to a prediction result of the probability for at least one of the plurality of classes; and causing an output device to output the prediction result and an indicator indicating the importance together with the measurement waveform.

Use of deep learning model has been attempted for determination on physiological information of a subject. On the other hand, when a deep learning model is used, it is theoretically difficult to obtain a clear basis for the prediction result. In the medical field, there is a tendency of avoiding ambiguous basis for determination.

According to the configuration according to each aspect described above, it is possible to use a convolutional neural network, which is a deep learning technique, for determination performed on physiological information, while visually presenting information that can serve as basis for prediction to a user through an indicator indicating which portion of the measurement waveform contributes to the determination, so that the user can be entrusted with interpretation or verification of the determination result. Therefore, it is possible to enhance interpretation of a processing result of the physiological information performed using the deep learning technique.

The invention claimed is:
1. A physiological information acquisition device configured to acquire physiological information of a subject, the physiological information acquisition device comprising:
an input interface configured to receive waveform data corresponding to a measurement waveform of the physiological information from a sensor;
a prediction unit configured to extract a feature from the waveform data using a convolutional neural network and predict a probability of the waveform data being classified into each of a plurality of classes;
an importance specification unit configured to specify an importance of the extracted feature with respect to a prediction result of the probability for at least one of the plurality of classes, the importance of the feature indicating a change in the prediction result of the probability attributable to the extracted feature; and
an output unit configured to output an indicator indicating the importance of the extracted feature together with the measurement waveform.

2. The physiological information acquisition device according to claim 1, wherein
the indicator is a color corresponding to the importance.

3. The physiological information acquisition device according to claim 1, wherein
the indicator is displayed in a manner overlapping the measurement waveform.

4. The physiological information acquisition device according to claim 1, wherein
the output unit is configured to output a first prediction result that is a prediction result of the probability for a first class included in the plurality of classes, and a second prediction result that is a prediction result of the probability for a second class included in the plurality of classes,
the importance specification unit is configured to specify a first importance that is an importance of the feature with respect to the first prediction result, and a second importance that is an importance of the feature with respect to the second prediction result, and
the indicator includes a first indicator indicating the first importance and a second indicator different from the first indicator and indicating the second importance.

5. The physiological information acquisition device according to claim 1, wherein
the output unit is configured to output a first prediction result that is a prediction result of the probability for a first class included in the plurality of classes, and a second prediction result that is a prediction result of the probability for a second class included in the plurality of classes,
the importance specification unit is configured to specify a first importance that is an importance of the feature with respect to the first prediction result, and a second importance that is an importance of the feature with respect to the second prediction result,
the indicator includes a first indicator indicating the first importance and a second indicator indicating the second importance, and
the first indicator and the second indicator are displayed in a manner without overlapping the measurement waveform.

6. A processing device configured to process physiological information of a subject, the processing device comprising:
an input interface configured to receive waveform data corresponding to a measurement waveform of the physiological information from a sensor; and one or more processors configured to:
- extract a feature from the waveform data using a convolutional neural network to predict a probability of the waveform data being classified into each of a plurality of classes;
- specify an importance of the extracted feature with respect to a prediction result of the probability for at least one of the plurality of classes, the importance of the extracted feature indicating a change in the prediction result of the probability attributable to the extracted feature; and
- cause an output device to output the prediction result and an indicator indicating the importance of the extracted feature together with the measurement waveform.

7. A non-transitory computer-readable recording medium storing a computer program for causing one or more processors to execute a process, the process comprising:
- receiving waveform data corresponding to a measurement waveform of the physiological information from a sensor;
- extracting a feature from the waveform data using a convolutional neural network to predict a probability of the waveform data being classified into each of a plurality of classes;
- specifying an importance of the extracted feature with respect to a prediction result of the probability for at least one of the plurality of classes, the importance of the extracted feature indicating a change in the prediction result of the probability attributable to the extracted feature; and
- causing an output device to output the prediction result and an indicator indicating the importance of the extracted feature together with the measurement waveform.

8. The physiological information acquisition device according to claim 1, wherein the extracted feature is a part of the waveform.

9. The processing device according to claim 6, wherein the extracted feature is a part of the waveform.

10. The non-transitory computer-readable recording medium according to claim 6, wherein the extracted feature is a part of the waveform.

* * * * *